United States Patent [19]
Tarnopolsky

[11] Patent Number: 5,104,505
[45] Date of Patent: * Apr. 14, 1992

[54] METHOD AND APPARATUS FOR ELECTROPHORETIC SEPARATIONS

[75] Inventor: Yuri Tarnopolsky, Narragansett, R.I.

[73] Assignee: Separations Technology, Inc., Wakefield, R.I.

[*] Notice: The portion of the term of this patent subsequent to Jul. 16, 2008 has been disclaimed.

[21] Appl. No.: 575,066

[22] Filed: Aug. 30, 1990

Related U.S. Application Data

[63] Continuation-in-part of Ser. No. 407,173, Sep. 14, 1989.

[51] Int. Cl.$^5$ .................. B01D 57/02; B01D 61/42
[52] U.S. Cl. ........................ 204/180.1; 204/299 R
[58] Field of Search ................ 204/299 R, 182.8

[56] References Cited

U.S. PATENT DOCUMENTS

4,048,049  9/1977  Hoefer ................ 204/299 R
4,284,491  8/1981  Vesterberg .......... 204/299 R Primary Examiner—John Niebling
Assistant Examiner—Caroline Koestner
Attorney, Agent, or Firm—Donald Brown; Peter F. Corless

[57] ABSTRACT

The present invention relates to electrophoresis. More particularly, the present invention relates to utilization of electrophoresis with controlled cooling. Still more particularly, the invention relates to a method and apparatus for separating chemical components in a solution in both a batch and a continuous mode.

44 Claims, 8 Drawing Sheets

METHOD AND APPARATUS FOR ELECTROPHORETIC SEPARATIONS

PRIOR APPLICATION

This application is a continuation-in-part of U.S. patent application Ser. No. 07/407,173, filed Sept. 14, 1989.

BACKGROUND OF THE INVENTION

The process of electrophoresis has gained notoriety in recent years as a method of performing difficult separations, particularly separations involving organic materials in solutions. Thus, in biochemical applications, for example, organic compounds such as peptides, proteins, nucleic acids, antibodies and the like may be separated in solutions containing them by the utilization of electrophoretic techniques. These techniques have generally involved the utilization of columns having tubes and packing and applying electrical charges to the tubes to electrically charge the components of the solution and separating them based on their electrical charge or stated another way on their electrophoretic mobility. A typical patent describing such a separation is U.S. Pat. No. 3,533,935.

In a similar vein attempts have been made to utilize capillary tubes for the purpose of conducting the electrophoretic separation. In these processes the separation is conducted inside of the tube. Typical examples of such operations are those described in U.S. Pat. Nos. 3,620,958 and 3,941,678.

One of the more serious problems encountered in conducting electrophoretic separations on a larger scale is the generation of heat caused by the electrical current passing across the tube or vessel filled with the electrolyte in which the electrophoresis is taking place. This requires special cooling techniques and a patent describing the problem associated with cooling and one system for conducting cooling is described in U.S. Pat. No. 4,177,130.

In order to overcome convection, various anti-convective media are used such as gels and porous membranes.

Gel electrophoresis has been utilized in the art by employing gels in an array of individual tubes. In general, these processes are of a batch nature and a typical process is shown in U.S. Pat. No. 4,747,919.

Porous membranes were used in PCT International Application No. 7900,942, for the purpose of preventing convection and streamlining the flow of the liquid in an electrophoretic separation.

However, anti-convective media make cooling inefficient and difficult. For this reason, the liquid undergoing separation is cooled typically outside the electrophoretic chamber, as shown in this PCT Application.

While the prior art has successfully demonstrated that electrophoresis can be conducted and that solutions containing multiple components can be separated utilizing these methods, difficulty has been encountered in translating that technology to a continuous phase operation so that the separations can be conducted continuously with the recovery of the components of a given solution being made on a continuous basis. Further, in scaling up prior art processes the art faces a major problem in that considerable heat, which is generated has to be dealt with effectively. If it is not, the separations attempted will not be effective due to the generation of convective currents in the electrophoretic chamber. Further, in the case of solutions containing thermally sensitive biochemical components, these components can be destroyed.

Thus, a need exists to provide electrophoretic systems that, while capable of conducting viable separations, provide easy heat removal even when the process is scaled up to separations of large quantities of material. The need to remove heat effectively from both batch and continuous electrophoretic separations also is present. It should be done in an effective and uncomplicated manner.

SUMMARY OF THE INVENTION

In accordance with the instant invention, an apparatus is provided, which is suitable for use in conducting electrophoretic separations. It is simple in construction and permits adequate removal of heat during the separation, so that the process can be conducted effectively on a batch or continuous basis. Still further, the invention provides a system that can be used for the continuous removal of the separated components of a liquid mixture undergoing electrophoresis, so that the components can be collected on a continuous basis separately. Finally, the apparatus and methods provide for sale up of electrophoresis equipment to any desirable, practical extent without the deleterious effects of inadequate heat removal being experienced.

While gel electrophoresis is known to be one of the basic methods of separation in biochemistry and molecular biology, it is hard to scale it up, because of the problem of heat dissipation. This invention overcomes this obstacle.

The method conducted in accordance with the instant invention involves a process in which the solution to be separated is passed through a chamber containing a plurality of closely packed hollow fibers. The fibers are packed in such a manner that interstitial spaces are provided in between the individual fibers, which are of sufficient value to permit the flow of liquid through the chamber by the application of sufficient head or pumping pressure. The solution to be separated is then pumped or passed from one end of the chamber to the other at a rate sufficient to prevent or minimize the formation of convection currents in the chamber. Means are also present to supply electric current across the reaction chamber containing the packed fibers at a satisfactory voltage gradient to cause the solutions flowing therein to separate due to the difference in the electrophoretic mobility of their constituents. Further means are provided to introduce heat exchange fluid through the center of the hollow fibers to thereby allow for the cooling continuously through the chamber during the electrophoretic separation. Modified buffered solutions of the materials undergoing separations may also be provided by introduction of these solutions with those undergoing separation in individual streams or through the cooling hollow fibers by making these fibers with semi-permeable walls and feeding buffer solutions thereto as a coolant and a pH control, and achieving thereby electrofocusing. The hollow fibers in accordance with this embodiment of the invention perform both cooling and anti-convective functions.

BRIEF DESCRIPTION OF THE DRAWINGS

The invention will now be described with reference to specific drawings in which.

DETAILED DESCRIPTION OF THE INVENTION

Figure 1:
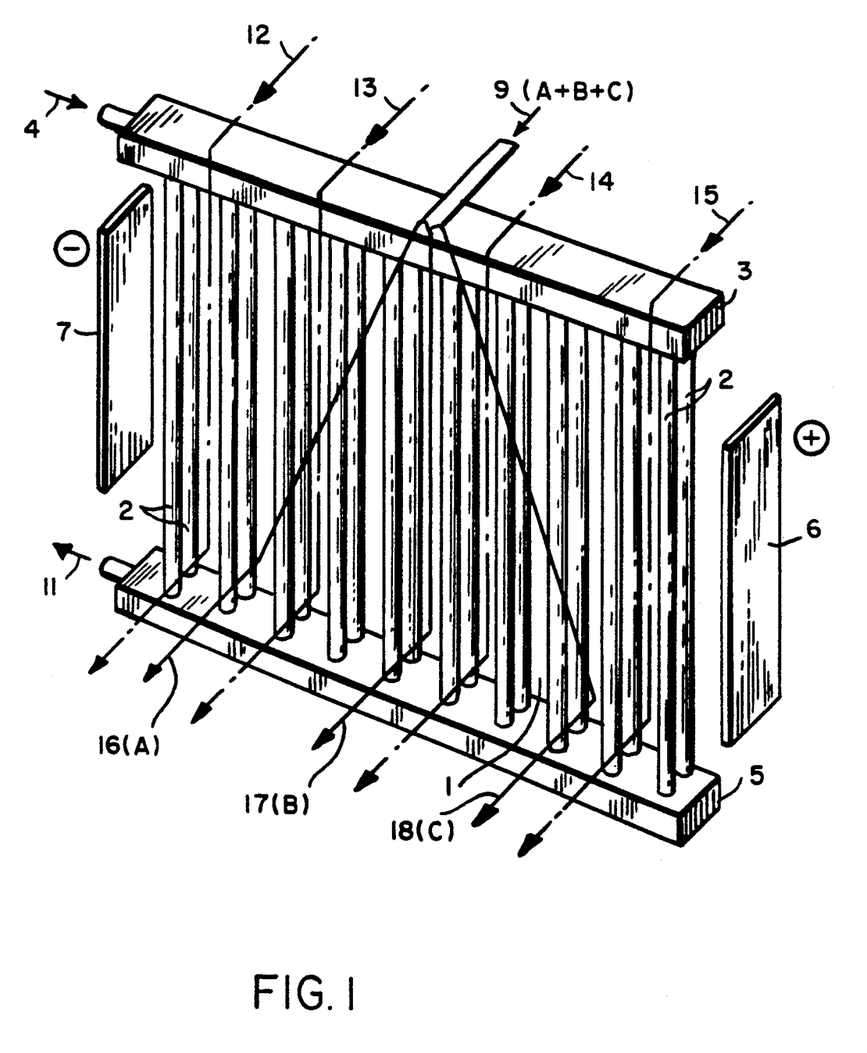
FIG. 1 shows a schematic diagram of the electrophoretic process conducted in accordance with the principles of the instant invention with the cooling tubes and electrodes being exaggerated in spacing for clarity in describing the process.

Turning to FIG. 1, there is shown an electrophoretic chamber generally indicated at 1. The chamber has a header 3 located at the top thereof, which has an inlet shown by the arrow 4 on the left hand side of the Figure. Connected to the header 3 and in communication with it are a plurality of hollow fibers 2, which terminate in a collection chamber 5 located at the bottom of the device. These fibers 2 are shown separated by large spaces between them for illustration purposes only. In reality, they are much closer together as will be obvious to the skilled artisan when FIG. 2 herein is discussed. The electrophoretic chamber 1 is also equipped with an anode 6 and a cathode 7 on either side of the chamber, and as indicated in the Figure, the solution to be treated flows through the device by passing it as indicated by the arrow 9 across the device from top to bottom as shown in the Figure in the interstitial spaces provided by the spacing of hollow fibers 2. The collection chamber 5 is provided with an exit 11. Also shown is the planar flow of buffer solutions to the chamber indicated by arrows 12, 13, 14 and 15 which contact solutions A, B and C. As the A, B and C solutions and buffer solutions pass through the chamber from the top to the bottom, necessary conductivity for the electrophoresis to take place is provided. By injecting buffer solutions of different pH values along the directions shown by the arrows 12 to 15, a pH gradient across the chamber can be created providing the necessary conditions for electrofocusing.

In the operation of the method in accordance with this system, solution containing material to be separated is introduced at the introduction point 9 shown in the FIG. 1 with the buffer solutions flowing at arrows 12, 13, 14 and 15. All the solutions are fed to the chamber continuously. In the chamber the solution A, B and C, which is a mixture, begins to separate upon the introduction of current at an appropriate voltage being applied between the anode 6 and the cathode 7 across the device 1 and the solution passing through it. This brings the particles of the components A, B and C into transversely directed motion based on their electrophoretic mobility causing them to separate. The components then are removed from the column on a continuous basis at the exit points 16 17 and 18.

Figure 2:
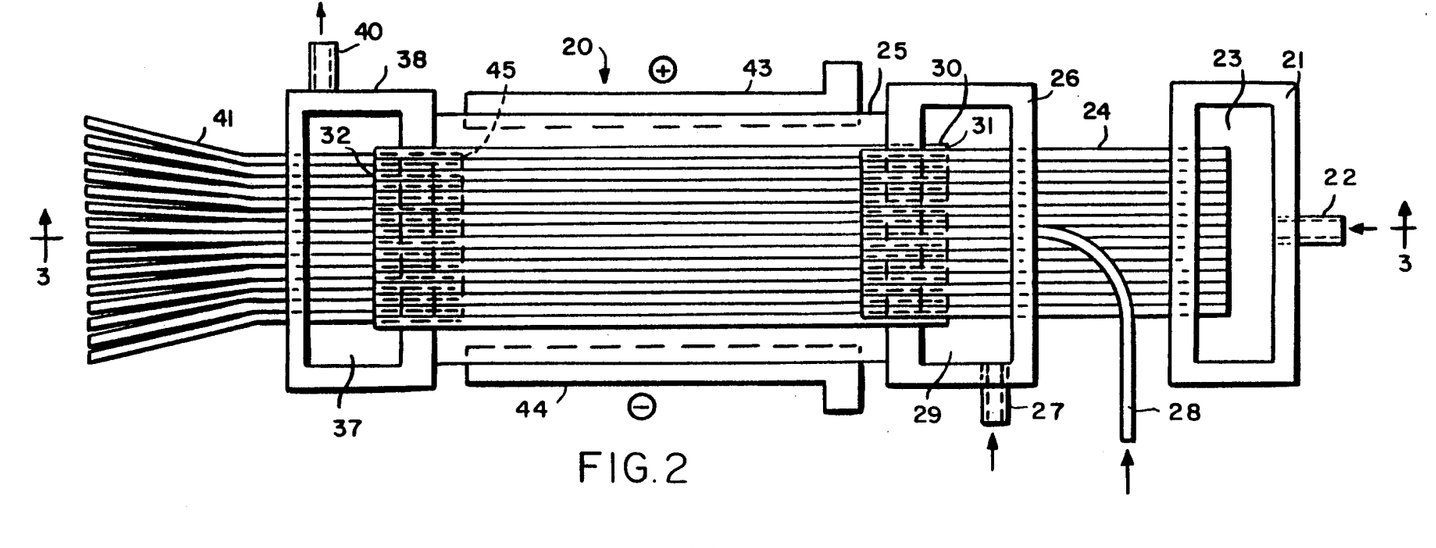
FIG. 2 shows a plan view of an apparatus suitable for use in conducting the electrophoresis process described herein.

Turning now to FIG. 2, an electrophoresis system is shown, which is generally indicated at 20. This system has container 21 with a chamber 23 and fluid inlet 22. A plurality of hollow delivery tubes 24 are positioned across the chamber 23. These tubes 24 terminate in the electrophoretic chamber 25 after passing through a second container 26, which has an inlet tube 27. The inlet 27 terminates in an internal chamber 29 located in container 26, which is also in communication with a plurality of closely packed hollow capillary tubes or fibers 30 (hereinafter "fibers") having one open end 31 in chamber 29 and the other open end 32 in chamber 37 of a third container 38. The inlet tube 28 terminates in chamber 25 like all of the tubes 24 so that the mixture of components to be separated can be injected into the common flow in chamber 25 through tube 28.

Figure 3:
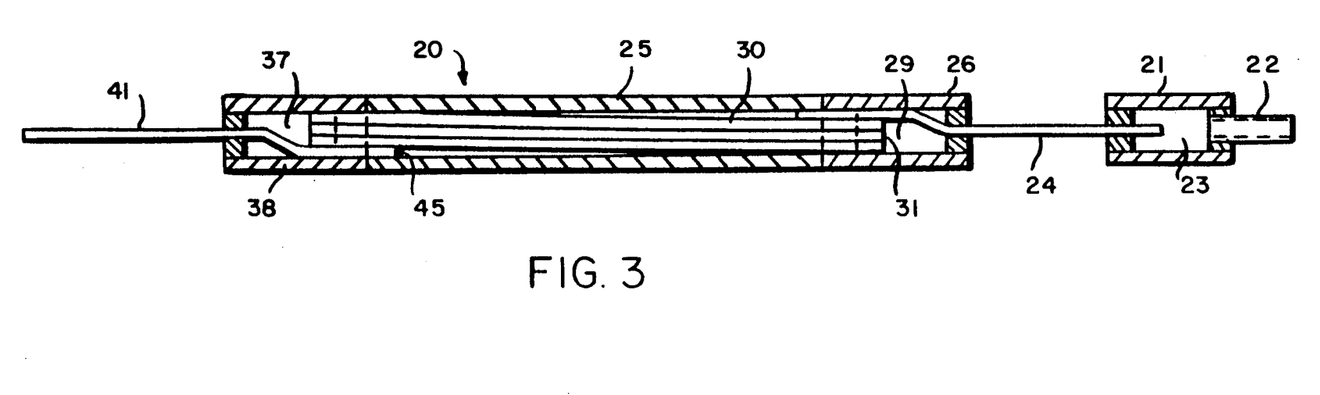
FIG. 3 is a cross section of FIG. 2 taken along the lines 3—3 of FIG. 2.

The cooling fluid introduced through inlet 27 is removed from the electrophoretic chamber 25 at exit 40 shown in the upper portion of the chamber 38 in FIG. 2. The fluid or solution introduced through inlet 22 is passed into chamber 25 where it passes with the mixture of components introduced by tube 28 through the chamber 25 to outlets 41 shown at the exit end of the electrophoretic chamber 25. As can be seen more clearly in FIG. 3, the buffer solution, which is introduced through tube 22 and passes through the hollow tubes 24 terminates at a point above the hollow fibers 30 located in the electrophoretic chamber 25 and thus, pass through that chamber in the interstices formed between the hollow fibers 30 in their packing width-wise and depth-wise throughout the chamber 25. The separated materials are removed through multiple outlets formed by the hollow tubes 41. The electrophoretic chamber 25 of the electrophoretic system 20 is also provided with an anode 43 and cathode 44 for the application of sufficient voltage to conduct the electrophoretic separation of the components.

In general, in operating the apparatus of FIG. 2, the buffer solution to be used, which can be any conventional buffer commonly employed to adjust pH, is introduced through inlet 22 and passes through the hollow tubes 24 into the electrophoretic chamber 25 in proximity to the fibers 30 shown therein. The buffer solutions fed through inlet 22 and tubes 24 are passed therethrough with sufficient head or pumping pressure to provide for continuous passage of the solutions in contact with and between the interstices of the capillary tubes 30 from one end of the electrophoretic chamber 25 to the other and with minimum turbulence being generated in the chamber 25. The solution to be separated is introduced in tube 28 to chamber 25 and, again, like the buffer solutions, is passed from one end of the chamber 25 to the other through the interstitial spaces provided by hollow fibers 30. The solution during its passage through chamber 25 is subjected to a D.C. voltage applied between anode 43 and cathode 44, which causes the material to separate into its components by virtue of differences in electrophoretic mobilities of each component. As the voltage is applied across the anode 43 and the cathode 44 and current passes through the chamber 25, the components of the solution introduced to the chamber 25 separate across the width of the chamber. The components, which are separated in accordance with their electrophoretic mobility, effectively separate into component streams.

As the solution being separated passes along the interstices of the hollow fibers 30, cooling fluid is introduced through inlet 27 into the inlet ends 31 of the hollow fibers 30 and is passed continuously along the long axis of the hollow fibers 30 into chamber 37 of the container 38 at open end 32 of the hollow fibers 30. This effectively removes the heat generated by the electrophoretic separation taking place as the solution to be separated passes through the chamber 25 and the heat exchange fluid is removed continuously through exit 40. Thus, the introduction and passage of the cooling fluid through fibers 30 and its removal at exit 40 is done on a continuous basis so that the chamber is continuously being charged with cooling solution at a regulated temperature. The heat evolution is thereby controlled, and the temperature control system eliminates overheating of the device during the passage of solutions through it. At the exit end of the electrophoretic chamber 25, a plurality of hollow tubes 41 are provided across the chamber 25, each having inlets 45 through which the separated components pass into some of the individual tubes shown. At the exit end of chamber 25, the inlets 45 of tubes 41 receive the separated components of the fee solution. The separated components may then be remove from the corresponding tubes 41.

The hollow fibers used for cooling may be of any convenient diameter. Preferably fibers having diameters in the range of 15 to 500 microns are used. The fibers have hollow interiors. In the preferred mode, hollow polymeric fibers are utilized.

Inorganic fibers such as hollow silica and hollow glass fibers are also suitable for this purpose. Exemplary of hollow glass fibers for use in this process are those described in U.S. Pat. Nos. 3,510,393, and more recently 4,735,642, the latter patent also describing in detail various glasses that may be utilized to form the hollow glass fibers.

Exemplary of the organic fibers, which are preferred as cooling fibers 30 are polymers such as polyethylene, polypropylene, polysulfones, polycarbonates, polyethylene terephthalate, polybutylene terephthalate, tetrafluoroethylene (Teflon ®) and other similar polymers capable of being made into hollow fibers.

In providing sufficient space in the interstices outside of and between the cooling fibers 30 usually the packing of the round fibers 30 themselves will suffice to provide it. If desired, however, recourse can be had to the use of spacers as long as they are permeable to fluid flow between the layers of fibers. These spacers can be between the fibers through the depth or width of the chamber 25 or both if desired. Suitable materials for this purpose are cloths, mats, scrims, meshes, filaments, membranes, papers and the like.

Electrodes 43 and 44 are usually housed in chamber 25 with a permeable membrane (not shown) positioned between the electrode surface and the contents of the chamber. Means (not shown) are also provided so that the electrodes can be rinsed continually with solution to remove the products of electrolysis from surrounding liquid. This is common practice in the art of which the skilled artisan will have knowledge. Solutions that can be separated into components in accordance with the instant invention are many and varied and the application of the various voltages will be determined, generally speaking, by recourse to the materials contained in the solution and their ability to separate based on their electrophoretic mobility.

In applying electric current across the solutions undergoing electrophoretic separation in accordance with the invention, the voltage utilized at a minimum is that voltage which will produce a separation in a given solution when applied across the chamber housing the solution. The maximum voltage utilizable is determined by safety factors and essentially has no bearing on the separation per se. In general, voltages of 50 to 200 volts per centimeter of distance between the electrodes (voltage gradient) are employed. A voltage gradient of 100 volts per centimeter has been found to be preferable and is used for most separations since this provides adequate separations for most solutions and minimizes safety risks.

EXAMPLES

In order to test the principles of the instant invention, a model was built which consisted of four flat chambers made of plexiglass and similar to the configuration shown in FIG. 2. Tap water was utilized as both buffer solution and the coolant in this Example, and it was introduced through inlets 27 and 22. A mixed water solution of amaranth (a red dye) and a blue food dye, which mixture has a violet color, was utilized as the mixture fed through inlet 28. Teflon ® spaghetti tubing having an internal diameter of 0.035 inches and an outside diameter of 0.097 inches was utilized as the tubes 24 and 41. The electrophoretic chamber 25 had dimensions of 4.5×2×0.125 inches. The electrodes were made of stainless steel mesh. They were separated from the solution in the main chamber by pieces of glass wool filter paper. No rinsing of the electrodes was provided during the experiment. The voltage applied between electrodes 43 and 44 during the test across the 2 inch width of the electrophoretic chamber 25 and 600 volts and the flow rate of the cooling fluid passing through the chamber was 100 milliliters/hour. The cooling tubes 30 were Teflon ® hollow fibers having the dimensions of 0.47 inches outside diameter and an internal diameter of 0.035 inches. When voltage was applied and the cooling tubes were operative, the violet track of the mixture was separated into three overlapping tracks. A red track formed on the anode side, a blue track formed on the cathode side and an intermediate track of a reduced violet color in between. When the cooling was stopped by deliberately cutting off the supply of water through inlet 27 during the test, the intermediate track was dominating, and bubbles of air or steam appeared between the cooling tubes. The electrophoretic chamber 25 was warm to the touch. While the mixture was being cooled with a continuous flow of coolant in tubes 30, the blue and red fractions separated readily and red fractions and blue fractions were collected continuously at the outlets of 41 separately from each other.

Many modifications of the invention can be made. Thus, using the device of FIG. 2, a separation can be enhanced by using a pH gradient across the electrophoretic chamber 25. For example, buffer solutions of differing pH values can be introduced into the inlets of tubes 24 individually. In this instance, the chamber 23, housing 21 and inlet 22 are no longer needed, since each of the tubes 24 will be fed directly with their own respective buffer solution, which solutions will have different pH values. Ampholytes such as proteins, for example, contain both anionic and cationic groups. Usually at some pH value such proteins will have no mobility in the electrophoretic (isoelectrical point) sense. Therefore, by controlling pH across the unit by segments, it is possible to concentrate the electrophoretic zone of an individual component along the pH gradient established between the electrodes by using as a control multiple buffer solutions of differing pH values. At some point along the gradient for example, one constituent will be isolated because it will have no mobility and in this way, by electrofocusing, made possible by the establishment of a given pH gradient across the chamber, that one component can be concentrated in a narrow band in the electrophoretic chamber and removed therefrom.

In another modification of the establishment of a pH gradient, the hollow fibers 30 can be formed of hollow glass or organic fibers that are semi-permeable or porous with a controlled porosity that imparts membrane properties to them. If fibers are used having these characteristics, buffer solutions can be introduced into fibers 30 via inlet 31, and the fibers will function as both a cooling tube and as a source of ions to establish a pH gradient across the chamber in the solutions being separated as they pass along the fiber surfaces. Again, each fiber will be fed buffers at various pH values.

Finally, if desired, the apparatus of FIG. 2 can be altered to conduct a batch process by moving electrodes 43 and 44 and placing them at the ends of chamber 25. Thus, for example, electrode 43 could be placed at the inlet end of chamber 25 and electrode 44 at the outlet end of chamber 25. In this instance, the separate inlet 28 is not necessary, since all solution is fed through inlet 22 and tube 24 to chamber 25. Cooling would still be done on a continuous basis, but the solution to be separated would be injected on a batch basis. The cross section of the electrophoretic chamber can be of any desirable shape, for example, round.

The preferred embodiment shown in FIGS. 4 through 9 will now be described.

This embodiment is preferably constructed of polycarbonate plastic.

Figure 4:
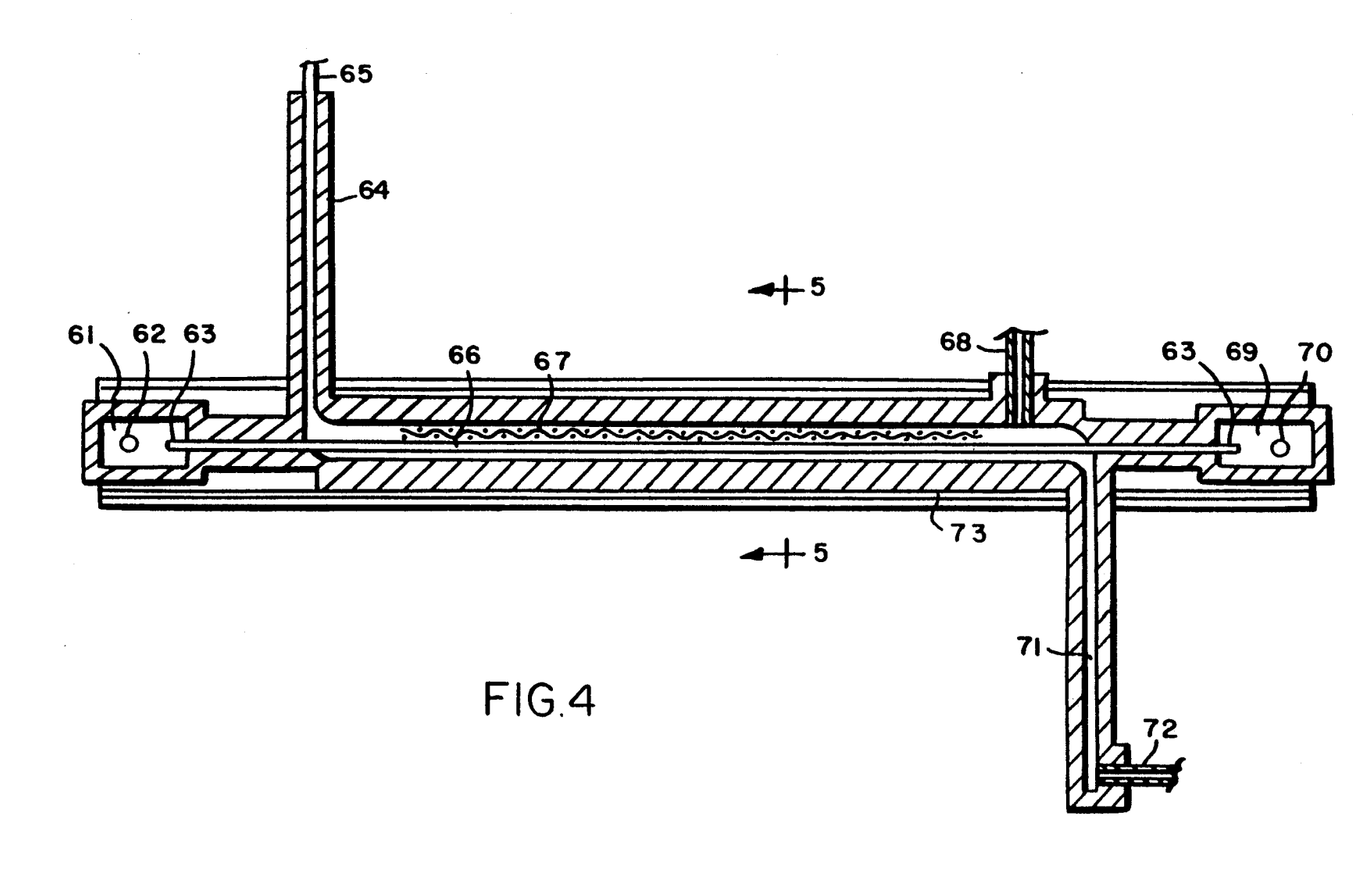
FIG. 4 is a sectional view of the preferred embodiment of the invention.
Figure 5:
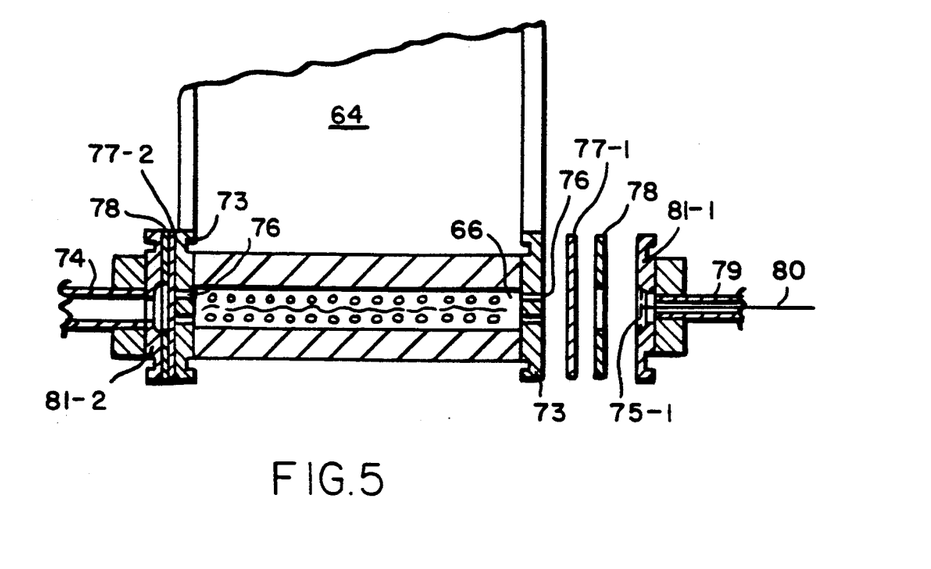
FIG. 5 is a sectional view taken along line 5—5 of FIG. 4, with certain parts separated.
Figure 6:
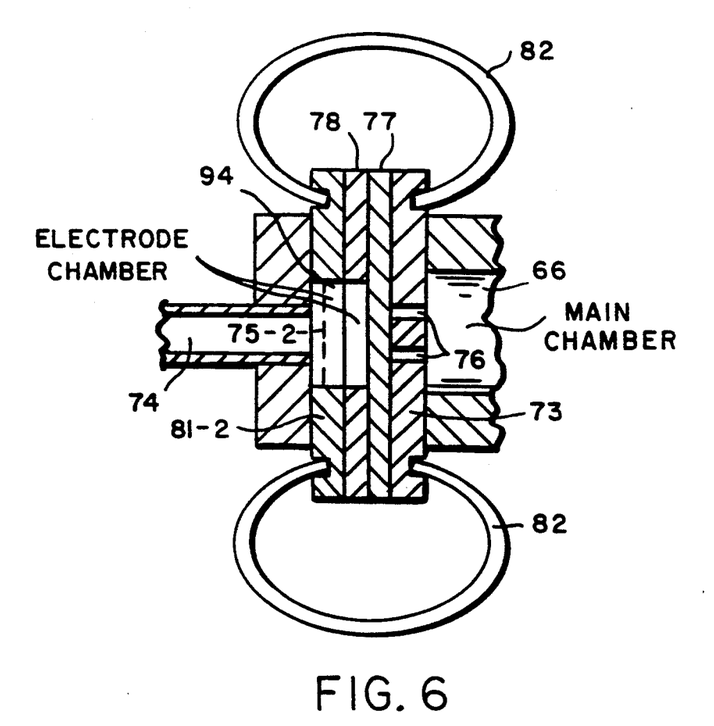
FIG. 6 is an exploded partial sectional view of a portion of FIG. 5.
Figure 7:
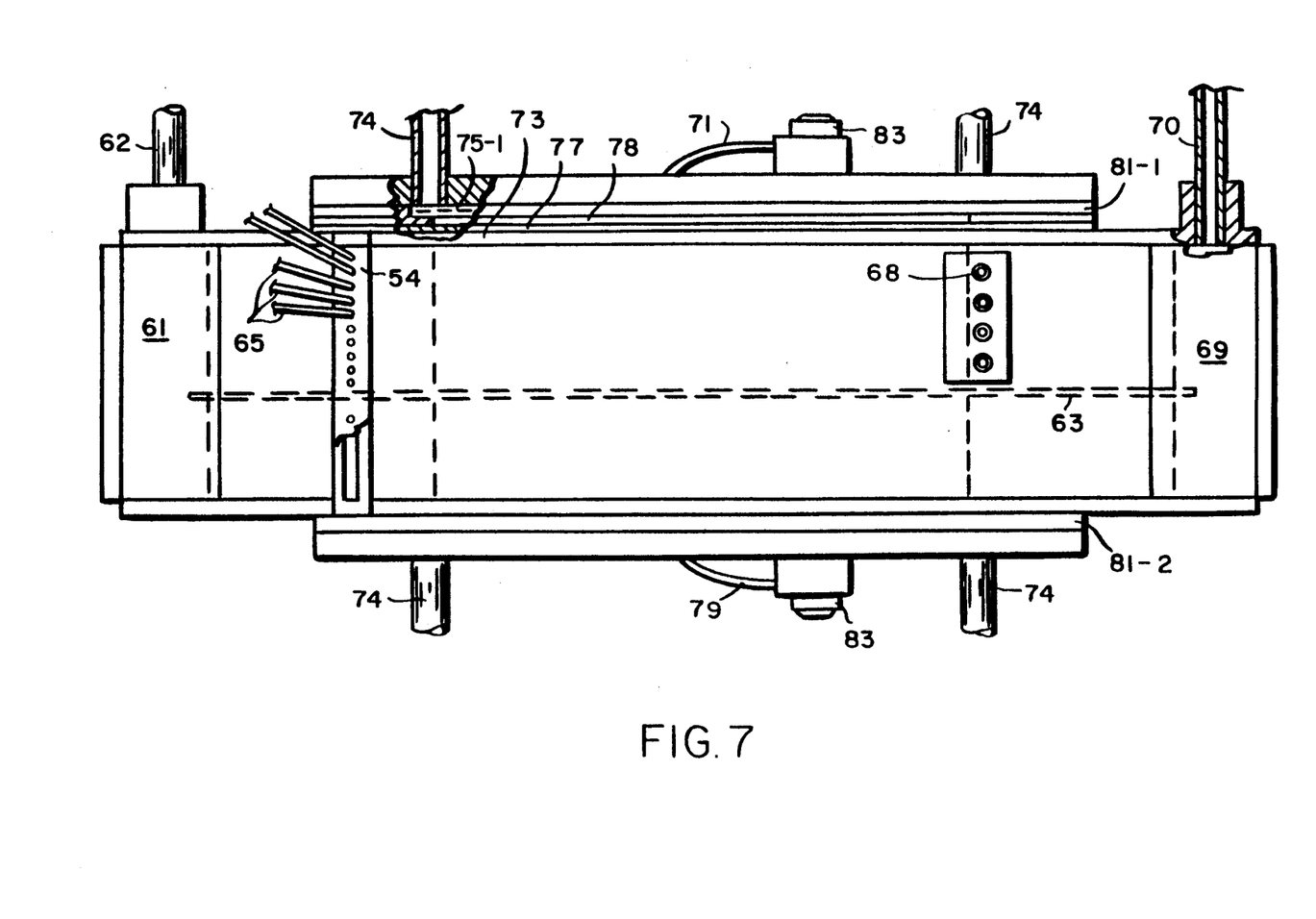
FIG. 7 is a detailed plan view of FIG. 4, partially sectioned.
Figure 8:
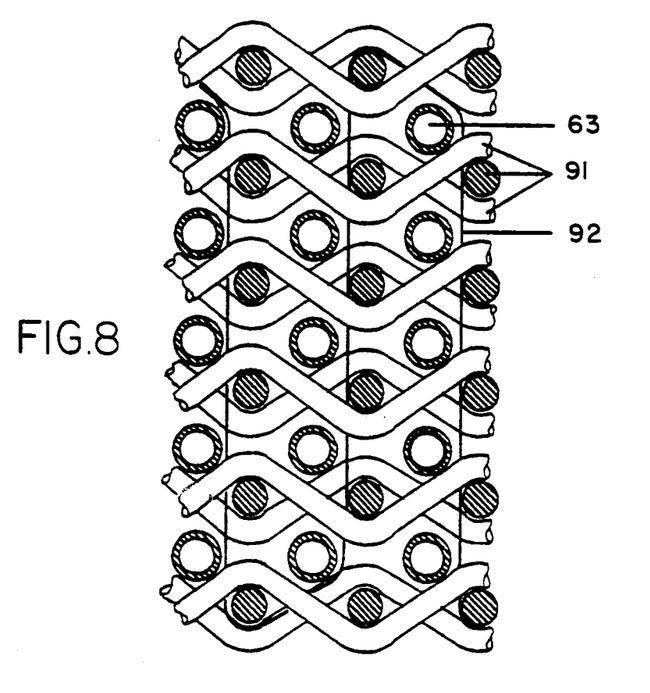
FIG. 8 is a schematic view of the arrangement of the tubes, the mesh and the thread showing 5 layers of tubes of the separation bed.

In particular, FIG. 4 shows the longitudinal cross-section of the main chamber, FIG. 5 presents a cross-section of the main chamber together with the electrode chambers taken along line 5—5 in FIG. 4, FIG. 6 is a more detailed picture of the assembly of the main and an electrode chambers. FIG. 7 is the plan view of the assembled system and FIG. 8 shows the mutual arrangement of mesh 91, tubes 63, and thread 92 in the separation bed.

In FIG. 4, there is inlet water chamber 61 with water inlet tube 62 and outlet water chamber 69 with water outlet 70. They are also shown in FIG. 7.

The electrode chambers 81-1 and 81-2 are separated from the main chamber by a porous membranes 77-1 and 77-2, see FIGS. 4 through 7. The membranes 77-1 and 77-2 prevents gas exchange between the chamber 66 and chambers 81-1 and 81-2. The electrode chambers are each coupled to the main chamber 66 through a gasket 78 and the slide-on lock 82, e.g., of synthetic plastic, see FIG. 6. Therefore, the membranes 77-1 and 77-2 and the mesh electrodes 75-1 and 75-2 can be easily inspected and changed. The electrodes 75-1 and 75-2 are inside the electrode chambers 81-1 and 81-2 respectively (see FIG. 7 where electrode 75-1 is shown in chamber 81-1).

The electrodes 75-1 and 75-2 extend the length of the chambers 81-1 and 81-2, respectively between tubes 74 (shown at top and bottom of FIG. 7).

Electrodes (see FIGS. 5 through 7), are preferably made of stainless steel mesh screen which is preferably placed perpendicular to the electric field so that the electric field is more uniform. Each electrode 75-1 and 75-2 are connected with the sockets 83 through the wires 80 (one for each electrode) encased in the tubes 79 (See FIGS. 5 and 7). A power cable (not shown) is connected to a power supply (not shown) for providing power to the electrodes.

The electrode chambers 81-1 and 81-2 have inlets and outlets 74, see FIGS. 5 through 7, for the rinsing electrolyte, which removes the products of electrodes.

The cooling tubes, 63 in FIGS. 4 and 7 (only one tube is shown), in the main chamber 66 are aligned and spaced with Teflon ® mesh so that they form a regular structure of a separation bed with approximately equal distances between the individual tubes. The plane of the mesh is parallel to the plane of the main chamber 66.

The structure of the alternating mesh and tubing is shown in

FIG. 8. The main chamber 66 preferably has five layers of tubing placed between six layers of mesh generally shown at 67. The mesh 91 and the tubing 63 are stitched together with a fine polymer thread 93.

The main chamber 66 is provided with carrier chamber, 71 (FIG. 4), which is positioned perpendicular to the main chamber.

The carrier inlet chamber has five inlets 72, (only one shown in FIG. 4), for injecting carrier electrolytes of different composition.

The carrier electrolyte changes the direction of the flow at direct angle when it enters the main chamber 66. The transition from the injection chamber 71 to the main chamber 66 is rounded for a better uniformity of the flow (See FIG. 4).

The main chamber has four sample injection ports (tubes), 68, see FIGS. 4 and 7. The injection tubes are located in one half of the chamber.

The sample is injected through a needle (not shown), which is inserted into the sample injection tube 68. The tip of the needle goes between the cooling tubes and stays in the main chamber. Regularly, only one injection point is used. Several injection points are present; thus, the position of the sample injection can be varied across the separation bed.

The main chamber has perforated plates, 73, see FIGS. 5 through 7, on its sides. The perforation, 76, FIGS. 5 and 6, provides electrical contact between the main and the electrode chambers. The membrane, 77, is placed between the perforated plate, 73, and the gasket, 78. The other side of the gasket is pressed by the electrode chamber.

The main chamber has the array of 44 outlets, shown at 65, see FIGS. 4 and 7, are preferably made of Teflon ® tubing. The flow in the main chamber changes direction at an angle when it enters the outlets. The transition from the main chamber to the outlets is preferably made rounded. Right after the main chamber, the outlets are sealed together in a flat plastic case shown at 64, see FIG. 4. Outside the case, 64, the outlets, 65, are not connected to each other. They end in a distribution plate (not shown).

The separation bed is preferably constructed of 5 layers of Teflon ® lightweight wall tubing 92, size 28, 30 capillaries in each layer. Tubing dimensions are, e.g.,: I.D. 0.015 inches, wall 0.006 inches. The layers are separated by Tetco TM woven mesh, Fluortex TM ETFE 9-590/47 and sewn together with Stren TM fishing line 0.008 inches. Parameters of the mesh are: Mesh opening, 590 μm (0.0232 inches); open area, 47%; mesh count, 29.5 per inch; thread O.D., 270 μm; fabric thickness, 425 μm.

Bed dimensions are by way of example: ¼×2 6/8×4½ inches.

The main and electrode chambers are preferably separated by MCI nylon membranes and by soft rubber gaskets compressed between flat surfaces by snap-on locks made of longitudinally cut Teflon ® tubes, O.D. ⅜ inches.

The sample mixture is injected through a needle with adjustable position of the tip.

Forty-four outlets (65) are made of lightweight wall Teflon ® tubes, size 24, I.D. 0.22, wall 0.006 inches. The outlets touch each other. They are sealed with silicone rubber between two plastic walls.

Using the apparatus shown in FIGS. 4 through 8, a separation of two proteins, such as cytochrome C and myoglobin was performed.

The starting mixture was prepared in the following way: 0.5 g bovine cytochrome C and 0.5 g horse myoglobin were dissolved in 100 ml of 0.125 g/l $K_2HPO_4$, pH 8.1, conductivity 159 μmhO/cm.

The following solutions were pumped by peristaltic pumps through the system of FIGS. 4 through 8:

A. The flow through carrier inlets numbered from anode to cathode was:

1. Mixture of 10 ml 1 g/l $KH_2PO_4$ and 990 ml 1 g/l $Na_2SO_4$, pH 4.0.

2., 3, and 4. 0.125 g/l $KH_2PO_4$ pH . 8.1.

5. Mixture of 100 ml 0.25 g/l $KH_2PO_4$, 900 ml 1 g/l $Na_2SO_4$, and 20 ml 4.5 g/l NaOH, pH 10.7.

Total flow rate through five channels was 3.37 ml/min.

B. The electrolyte in both electrode chambers was 1 g/l $Na_2SO_4$.

Total flow rate through two electrode chambers was 2 ml/min.

C. The flow rate of the sample was 0.17 ml/min (10 ml/hr); This flow rate corresponds to the throughput of proteins 0.1 g/hr.

The separation was conducted at 400 V, and 0.05 A.

The temperature of the cooling water was 9.3 degrees, the difference between the temperatures at the inlet and the outlet of water was 0.6 degrees at the flow rate 1 l/min.

The components of the mixture were successfully separated. Forty fraction were collected, of which thirty-six were analyzed by HPLC with the Varian 5500 Chromatograph.

At the conditions of the analysis, the cytochrome C peak occurs at a retention time of about 15.8 minutes. Two myoglobin peaks are observed at about 18.7 minutes and 22.9 minutes.

Figure 10:
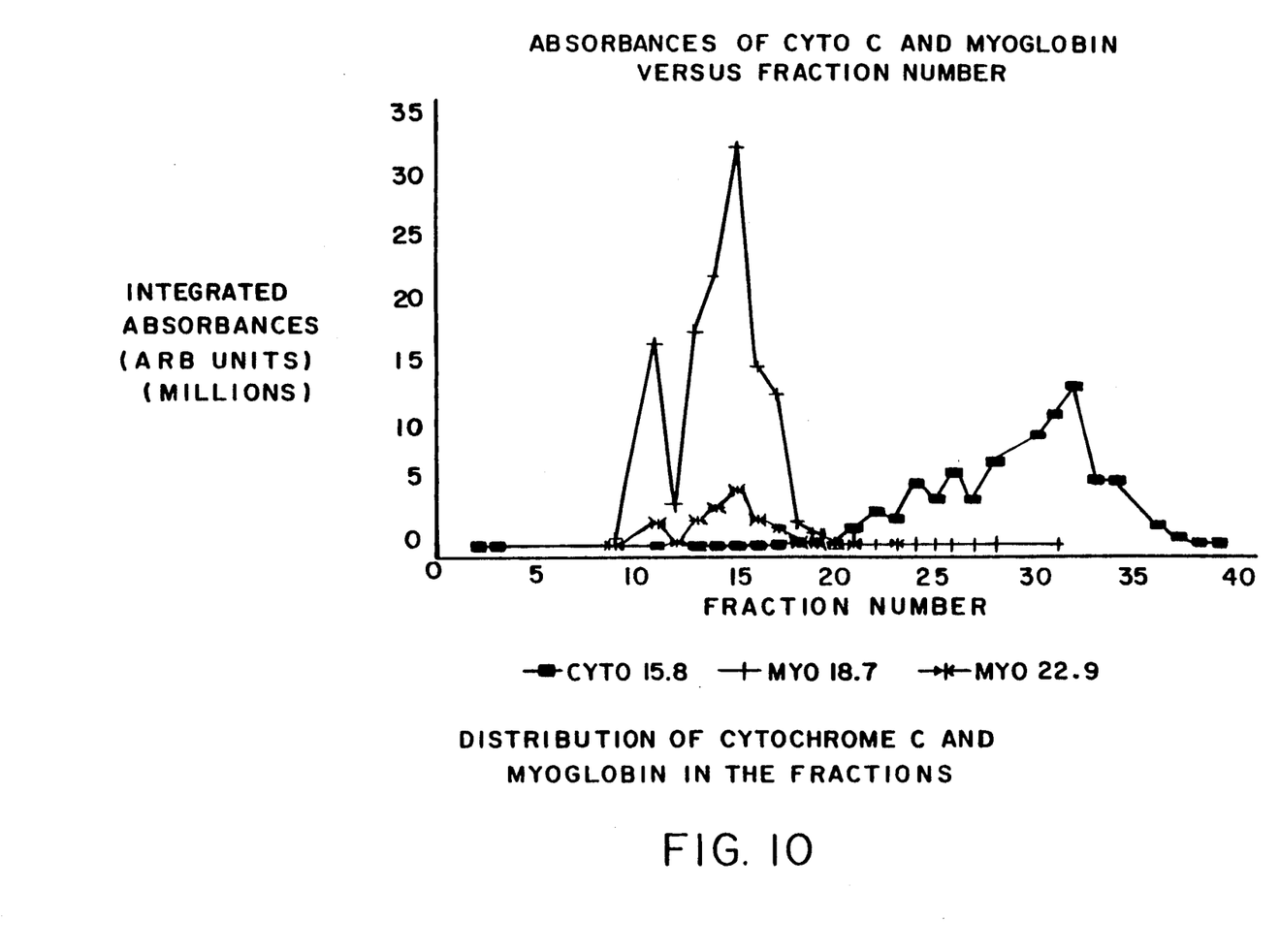
FIGS. 10 and 11 are graphs showing the results obtained using the apparatus of FIGS. 4 through 8.

Cytochrome C levels were found in Fractions 13-39. However, significantly higher levels are found in Fractions 21-36. Myoglobin is found in Fractions 9-31, with significantly higher levels found in Fractions 11-18. These results are plotted in FIG. 10.

Figure 11:
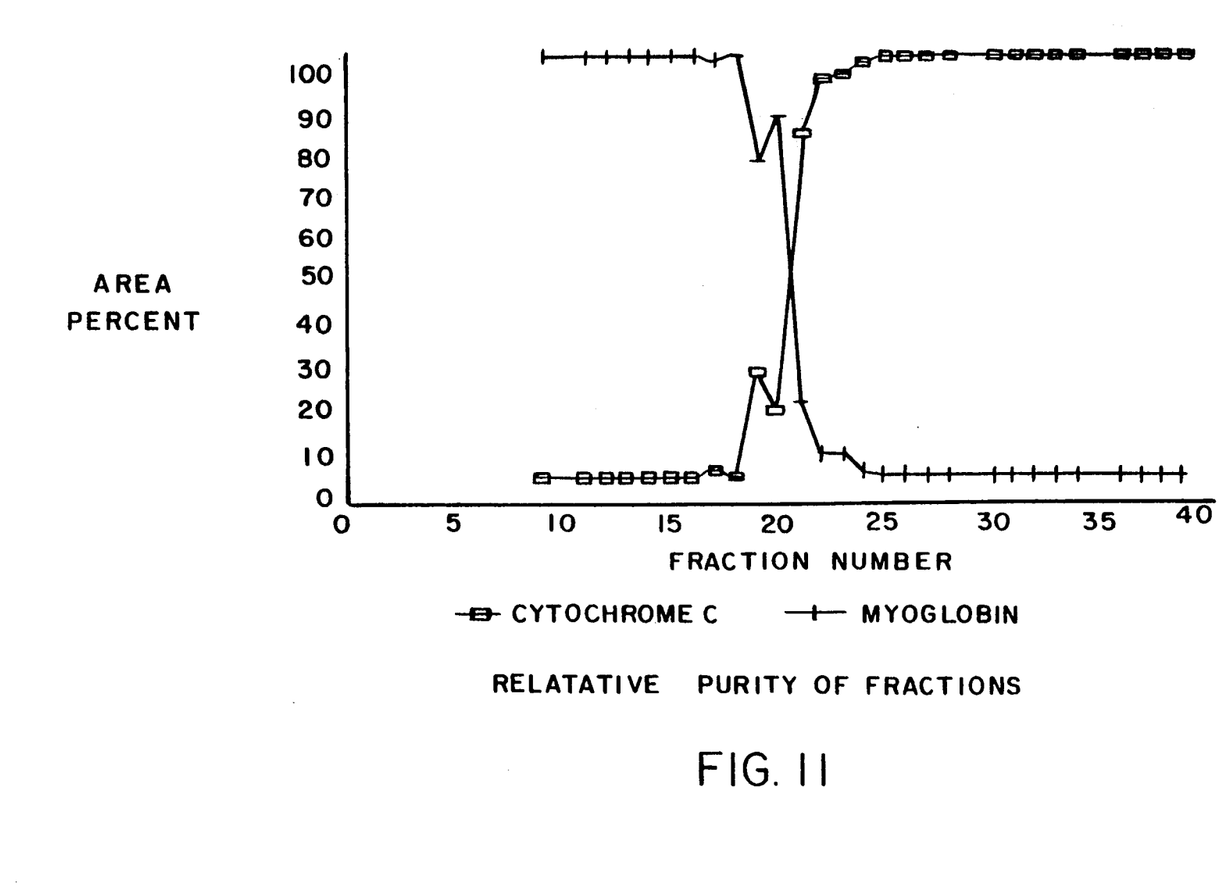

To quantify the purity of each protein in each fraction, the area percents of Cytochrome C and myoglobin were determined using the cytochrome C peak near 15.8 minutes and the myoglobin peak near 18.7 minutes. These results are plotted in FIG. 11. Myoglobin in purity greater than 99 area percent is found in Fractions 9-18. Cytochrome C is purity greater than 99 area percent is found in Fractions 25-39. As seen in FIG. 11, this represents a very high recovery of high purity myoglobin and a moderately high recovery of high purity cytochrome C. The recovery of cytochrome C may be improved through the use of electrofocusing or other techniques.

For the purpose of conducting the separation in gel media in the batch mode, the internal space of the main chamber can be filled with a gel such as agarose gel, polyacrylamide gel, or similar. The gel is introduced in the form of its liquid precursor, which solidifies due to chemical or thermal changes, according to well known procedures.

Figure 9:
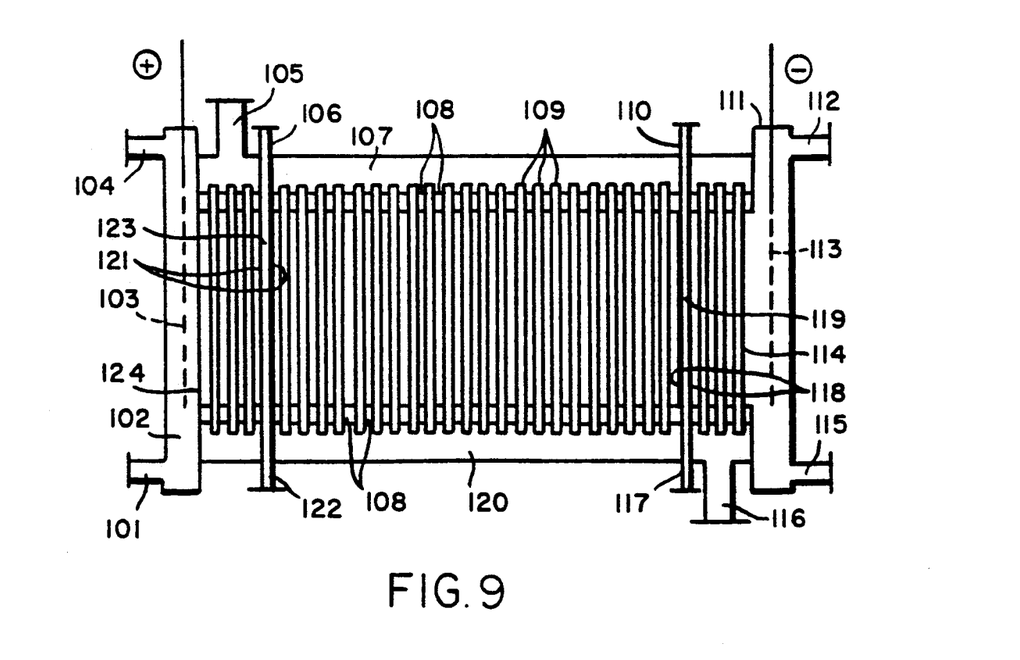
FIG. 9 is a plane view of an apparatus for gel electrophoresis.

The apparatus on FIG. 4 is modified in order to provide means for injecting the mixture and removing the components as shown in FIG. 9.

In particular, FIG. 9 shows a horizontal plane view of a longitudinal cross section of an apparatus for gel electrophoresis for use in the batch mode, according to this invention. The transversal cross section may be rectangular in shape.

The apparatus has an array of several layers of cooling tubes, 109. FIG. 9 shows only one layer of tubes. Together with two collector chambers 107 and 120, they form a heat exchanger. The apparatus is provided with inlet, 116, and outlet 105, for the cooling water. Two seals, 108, separate the collector chambers, 107 and 120, from the intersticial space between tubes 109. The interstitial space is separated from electrode chambers, 102 and 111, by membranes, 114 and 124, which are similar to the membranes 77 in FIGS. 5 through 7.

Another set of similar membranes, 118 and 121 form narrow injection chamber, 123, for injection the mixture, and a similar collecting chamber, 119, for removing the separated components.

The apparatus is filled with a liquid precursor of a gel when its top lid (not shown) is removed. The precurser solidifies with time.

The collection and injection chamber as well as electrode chambers preferably have the same design and they can be used interchangeably, depending on the direction of migration of the components. The injection chamber can be placed in the middle of the apparatus, and two collection chambers can be placed laterally.

For example, the mixture can be loaded through inlet, 122, and outlet, 106, and the components could be collected by washing them away through inlet, 117 and outlet, 110, with an appropriate solution.

The electrode chambers, 102 and 111, contain electrodes, 103 and 113. The electrode chambers have inlets, 101 and 115, and outlets, 104 and 112, for rinsing the electrodes with an appropriate electrolyte and removing the products of electrolysis.

The tubes, 109, can be spaced and aligned with special means, like on FIGS. 4 through 8, or just kept in place by seals, 108.

The whole interstitial space between membranes, 121 and 114, should be filled with gel, except the injection and collection chambers, 119, and 123. The membranes, 118, 114, 121, and 124, prevent the liquefied gel from penetrating the chambers 102, 111, 119, and 123, before the gel solidifies.

In the process of separation, the components are moving in the electric field from the injection chamber to the collection chamber with different mobilities, and they are eluted from the collection chamber at different times.

The membranes 114, 118, 121, and 124 can be made of any non-conductive porous material, for example, cellulose acetate, nylon, ceramics, etc. Dialysis membranes are suitable for that purpose, too.

In general, in an electrophoretic separation, according to this invention, there are three selected directions:

A. Direction of the electrical current.
B. Direction of the buffer flow (except for gel electrophoresis).
C. Direction of the coolant flow.

In the preferred embodiment shown in FIGS. 4 through 8, the coolant flow and the buffer flow are parallel while the electrical current is perpendicular to both of them.

However, according to this invention, other mutual orientations of the three directions are possible, as well. For example, an embodiment is possible with all three directions mutually perpendicular, so that the cooling tubes go through both larger walls of the main chamber. The advantage of the preferred embodiment is that the process of separation can be easily monitored through the transparent walls of the chamber. However, the above mentioned alternative embodiment allows for a simpler design of the buffer inlets and outlets, without changing the direction of the buffer flow.

While the invention has been described with reference of certain specific illustrative embodiments, it is not intended to be limited thereby except insofar as appears in the accompanying claims.

I claim:

1. A method of conducting an electrophoretic separation in a solution which is cooled by a cooling fluid to produce separated constituents from the solution comprising passing the solution into a chamber having a plurality of closely packed hollow fibers therein, causing the solution to flow in the chamber, providing on the outside of the fibers and between them sufficient interstitial space so that the solution can freely flow from the inlet of the chamber to the outlet thereof across the interstices and between the hollow fibers, passing cooling fluid through the interior of the hollow fibers while the separation is being conducted, passing electrical current through the chamber and the solution to thereby cause the constituents in the solution to separate into distinct and separate components and removing the separated components from the chamber at a point remote from the inlet.

2. The method of claim 1 wherein the solution and cooling fluid are fed continuously through the chamber during the separation, and the components are removed continuously.

3. The method of claim 1 where the hollow fibers are selected from the group consisting of organic fibers, inorganic fibers and mixtures thereof.

4. The method of claim 2 wherein the hollow fibers are selected from the group consisting of organic fibers, inorganic fibers or mixtures thereof.

5. The method of claim 3 wherein the hollow fibers are organic fibers.

6. The method of claim 3 wherein the hollow fibers are inorganic fibers.

7. The method of claim 4 wherein the hollow fibers are organic fibers.

8. The method of claim 4 wherein the hollow fibers are inorganic fibers.

9. The method of claim 1 wherein the electrical current is passed in a direction substantially normal to the flow of the solution passing through the chamber in the interstitial spaces.

10. The method of claim 2 wherein the electrical current is passed in a direction substantially normal to the flow of the solution passing through the chamber in the interstitial spaces.

11. The method of claim 3 wherein the electrical current is passed in a direction substantially normal to the flow of the solution passing through the chamber in the interstitial spaces.

12. The method of claim 4 wherein the electrical current is passed in a direction substantially normal to the flow of the solution passing through the chamber in the interstitial spaces.

13. The method of separating organic components from each other in solutions containing more than one organic substance to be separated comprising feeding the solution to be separated through an inlet into a separation chamber, flowing the solution from the inlet end of the chamber to an outlet end, providing in the chamber along the path of flow of the solution a plurality of closely packed hollow fiber tubes having their major axis aligned substantially parallel to the flow of the solution through the chamber, flowing heat exchange fluid through the hollow fibers in the chamber from one end to the other, passing the solution along the outer surfaces of the fibers and along the interstitial spaces between the fibers while passing current through the solution continuously at sufficient amperage and voltage to cause the components of the solution to separate from each other in their path of travel through the chamber and recovering the components from the solution so separated in separate streams at the exit end of the chamber.

14. The method of claim 13 wherein the solutions are buffered.

15. The method of claim 13 wherein the current is passed through the chamber in a direction substantially normal to the path of travel of the solution.

16. The method of claim 13 wherein the hollow fibers are selected from the group consisting of organic fibers, inorganic fibers or mixtures thereof.

17. The method of claim 14 wherein the hollow fibers are selected from the group consisting of organic fibers, inorganic fibers, and mixtures thereof.

18. The method of claim 15 wherein the hollow fibers are selected from the group consisting of organic fibers, inorganic fibers and mixtures thereof.

19. The method of claim 16 wherein the hollow fibers are organic fibers.

20. The method of claim 16 wherein the hollow fibers are inorganic fibers.

21. The method of claim 16 wherein the hollow fibers are glass fibers.

22. The method of claim 17 wherein the hollow fibers are organic fibers.

23. The method of claim 17 wherein the hollow fibers are inorganic fibers.

24. The method of claim 17 wherein the hollow fibers are glass fibers.

25. The method of claim 18 wherein the hollow fibers are organic fibers.

26. The method of claim 18 wherein the hollow fibers are inorganic fibers

27. The method of claim 18 wherein the hollow fibers are glass fibers.

28. The method of separating constituents in solution by electrophoresis comprising passing the solution to be separated into a chamber having a plurality of closely packed hollow fibers therein; flowing the solution to be separated along the major axis of the hollow fibers on the outside of the fibers in the interstitial spaces thereof in a plurality of streams, passing cooling fluid through the interior of the hollow fibers while the separation is being conducted, passing individual streams of buffer solutions at different pH values to each of the plurality of streams passing through the chamber and undergoing separation to thereby establish a pH gradient in the streams across the chamber, passing electric current through the chamber to cause the constituents of the which are amphoteric to separate in the form of narrow bands due to the focusing effect of the pH gradient established and removing the constituents so separated in individual streams.

29. In the method of claim 27 the improvement comprising feeding the buffer solutions into the hollow fibers, the hollow fibers having semi-permeable membrane walls.

30. A process for separating solutions using electrophoresis comprising feeding the solution to be separated through a chamber, packing the chamber with elongated hollow fibers having semi-permeable walls, the fibers being packed to provide in their interstices a plurality of passages for the fluid to be separated to flow between the hollow fibers during the separations, the cooling fluid being buffered to provide differing pH values across the chambers as said pass through the walls of the hollow fibers into the solutions undergoing separation to thereby provide a pH gradient across the chamber and introducing electric current through the chamber at sufficient voltage to separate the constitutes of the solution being separated into separate streams for collection.

31. An electrophoretic separation bed comprising a plurality of hollow fibers aligned and spaced, means to introduce fluid through said fibers, the packing of the fibers being arranged to provide sufficient space therebetween to permit the solution to be separated to flow in the interstices provided between the fibers by the packing.

32. The bed of claim 31, including spacers located between the fibers in the horizontal direction across said bed, said spacers being permeable to fluid flow.

33. The system of claim 31 wherein spacers are provided between the fibers in the vertical direction in the bed, the spacers being permeable to fluid flow.

34. The system of claim 31 wherein spacers are provided between the fibers in the horizontal and vertical directions in the bed, the spacers being permeable to fluid flow.

35. The system of claim 32 wherein the spacer is selected from the group consisting of cloth, mats, scrims, meshes, filaments, permeable membranes and papers.

36. The system of claim 33 wherein the spacer is selected from the group consisting of cloth, mats, scrims, meshes, filaments, permeable membranes and papers.

37. The system of claim 34 wherein the spacer is selected from the group consisting of cloth, mats, scrims, meshes, filaments, permeable membranes and papers.

38. The system of claim 31 wherein the fibers having external diameters of 10 to 500 microns.

39. The method of claim 1 in which the solution is caused to flow through the interstices along the major axis of the hollow fibers in the chamber.

40. The method of claim 1 wherein a solution is introduced into the interstitial space between the hollow fibers, and after having filled the chamber the said solution turns into gel so that the electrophoretic separation is conducted in a gel, the gel being cooled by the cooling fluid in the hollow fibers.

41. The method of claim 40 wherein the chamber has means to introduce the mixture and to remove components through compartments which have inlets and outlets, said compartments being separated from the gel by porous membranes, so that the compartments do not contain gel inside and allow for free flow of liquids.

42. The method of claim 1 wherein the hollow fibers have rough or corrugated outer surface-so that they can touch each other without obstructing electrical conductivity across the pack of the said fibers.

43. The method of claim 40 wherein the hollow fibers are oriented parallel to the electrodes and two pairs of additional flat semi-permeable membranes are positioned in the interstitial space between the hollow fibers and parallel to the electrodes, at a distance from the electrodes and from each other that the membranes form, together with the walls of the chamber, two closed compartments, the compartments being unaccessible to the gel and provided with inlets and outlets, to introduce a mixture into one of the compartments prior to electrophoretic separation, and to continuously wash out the components which are separated in the electric field along the way from one compartment to the other, the entire chamber being filled with gel, except the closed compartments, which are filled with electro-conductive liquid.

44. The method of claim 1 wherein the hollow fibers have rough or corrugated outer surface, so that when they are packed tightly into the chamber, the contacting outer surfaces form multiple fissures and clefts which insure sufficient hydraulic and electrical communication between the interstices in the absence of spacers in the pack of the said fibers.

* * * * *